United States Patent
Zhang et al.

(10) Patent No.: US 12,068,060 B2
(45) Date of Patent: Aug. 20, 2024

(54) RECORD FINDING USING MULTI-PARTY COMPUTATION

(71) Applicant: KONINKLIJKE PHILIPS N.V., Eindhoven (NL)

(72) Inventors: Lu Zhang, Eindhoven (NL); Meilof Geert Veeningen, Eindhoven (NL); Peter Petrus van Liesdonk, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 926 days.

(21) Appl. No.: 17/051,495

(22) PCT Filed: Apr. 22, 2019

(86) PCT No.: PCT/EP2019/060252
§ 371 (c)(1),
(2) Date: Oct. 29, 2020

(87) PCT Pub. No.: WO2019/211111
PCT Pub. Date: Nov. 7, 2019

(65) Prior Publication Data
US 2021/0366584 A1    Nov. 25, 2021

Related U.S. Application Data

(60) Provisional application No. 62/664,358, filed on Apr. 30, 2018.

(51) Int. Cl.
*G06F 16/00* (2019.01)
*G06F 16/14* (2019.01)
(Continued)

(52) U.S. Cl.
CPC ............ *G16H 10/60* (2018.01); *G06F 16/14* (2019.01); *G06F 16/148* (2019.01); *G06F 16/24* (2019.01);
(Continued)

(58) Field of Classification Search
CPC ........ G16H 10/60; G16H 50/70; G06F 16/14; G06F 16/148; G06F 16/24; G06F 16/245;
(Continued)

(56) References Cited

U.S. PATENT DOCUMENTS 8,281,148 B2   10/2012   Tuyls et al.
9,443,092 B2    9/2016   Nawaz et al.
(Continued)

FOREIGN PATENT DOCUMENTS

WO    2016178655 A1    11/2016

OTHER PUBLICATIONS

International Search Report and Written Opinion for International Application No. PCT/EP2019/060252, filed Apr. 22, 2019, 14 pages.
(Continued)

*Primary Examiner* — Alex Gofman
*Assistant Examiner* — Suman Rajaputra

(57) ABSTRACT

Some embodiments are directed to a requesting device and a data device configured for multi-party computation to select a close record from a database. The data device performs a filtering of its candidate records by selecting candidate records from the database for which a received set of similarity values for a target record are close to a set of similarity values for a candidate record. For one or more selected candidate records, the requesting device and the data device performing a multiparty computation protocol to jointly compute a second closeness measure between the target record and the selected candidate record.

13 Claims, 6 Drawing Sheets

(51) Int. Cl.
  *G06F 16/24* (2019.01)
  *G06F 16/245* (2019.01)
  *G06F 16/2455* (2019.01)
  *G06F 16/33* (2019.01)
  *G06F 16/35* (2019.01)
  *G06F 16/83* (2019.01)
  *G06F 16/835* (2019.01)
  *G06F 16/903* (2019.01)
  *G06F 16/9032* (2019.01)
  *G06F 16/906* (2019.01)
  *G16H 10/60* (2018.01)
  *G16H 50/70* (2018.01)

(52) U.S. Cl.
  CPC ........ *G06F 16/245* (2019.01); *G06F 16/2455* (2019.01); *G06F 16/33* (2019.01); *G06F 16/3331* (2019.01); *G06F 16/334* (2019.01); *G06F 16/35* (2019.01); *G06F 16/83* (2019.01); *G06F 16/835* (2019.01); *G06F 16/903* (2019.01); *G06F 16/9032* (2019.01); *G06F 16/90335* (2019.01); *G06F 16/906* (2019.01); *G16H 50/70* (2018.01)

(58) Field of Classification Search
  CPC .. G06F 16/2455; G06F 16/33; G06F 16/3331; G06F 16/334; G06F 16/35; G06F 16/83; G06F 16/835; G06F 16/903; G06F 16/9032; G06F 16/90335; G06F 16/906
  See application file for complete search history.

(56) References Cited

U.S. PATENT DOCUMENTS

| | | | |
|---|---|---|---|
| 2012/0143922 A1 | 6/2012 | Rane et al. | |
| 2014/0082006 A1* | 3/2014 | Knight | G06F 16/325 707/758 |
| 2014/0279757 A1* | 9/2014 | Shimanovsky | G06F 16/2379 706/12 |
| 2018/0114028 A1* | 4/2018 | Kafai | G06F 16/24578 |
| 2020/0372079 A1* | 11/2020 | De Vries | G06F 16/906 |

OTHER PUBLICATIONS

Plasensia-Calana, et al., "Selecting feature lines in generalized dissimilarity representations for pattern recognition", Digital Signal Processing, vol. 23, Issue 3, May 2013, pp. 902-911. (Abstract).

Lindell, et al., "Secure Multiparty Computation for Privacy-Preserving Data Mining", Journal of Privacy and Confidentiality, May 6, 2008, pp. 1-39.

Plasencia-Calana, et al., "Towards cluster-based prototype sets for classification in the dissimilarity space", CIAR2013, 093, V.1, pp. 1-8.

Platt et al., "Probabilistic Outputs for Support Vector Machines and Comparisons to Regularized Likelihood Methods", Advances in large margin classifiers, 10(3): Mar. 26, 1999, pp. 1-11.

* cited by examiner

RECORD FINDING USING MULTI-PARTY COMPUTATION

RELATED APPLICATIONS

This application is the U.S. National Phase application under 35 U.S.C. § 371 of International Application No. PCT/EP2019/060252, filed on Apr. 22, 2019, which claims the benefit and priority to Provisional Application No. 62/664,358, filed Apr. 30, 2018. These applications are hereby incorporated by reference herein, for all purposes.

FIELD OF THE INVENTION

The invention relates to a requesting device, a data device, a requesting method, a data method and a computer readable medium.

BACKGROUND

At many locations, large amounts of data are being collected. Businesses collect information regarding their products, their clients, and so. Schools collect information regarding their curricula or students. Hospitals collect data on their patients. Such data can be put to good use, e.g., because current situations can be compared to historic cases so that more information is available. Nevertheless, for rare cases it is still desirable that a record on one computer can be compared to records stored on another computer.

As a motivating example, we will consider the situation in which patient records are compared, e.g., to find different patients that are suffering from the same rare disease. However, as said, similar problems occur in other fields. Finding similar cases of a disease is also important, e.g., for monitoring population health by screening for a certain disease.

Labeling records with diseases, e.g., assisted with supervised or unsupervised learning applied to the data set, is not a satisfactory solution. Especially for rare diseases, in which finding records at other hospitals is most desired, labelling is likely not to work well, since few records are available for the label.

Finding similar cases of a rare disease from external sources is challenging, and the challenges mainly come from the patient privacy. We use requesting hospital to indicate the hospital which is looking for similar cases of a rare disease; we use target record to indicate the record for which we want to find similar cases, and data hospitals to indicate the external sources.

In a first option, the requesting hospital sends out the target record to the data hospitals; or the data hospitals give access to their records to the requesting hospital. In this case, either the requesting or the data hospitals can use their own model, e.g., their own clustering model to compare records, and find similar cases.

In a second option, the requesting hospital and data hospitals use multi-party computation (MPC) together to find similar cases. In this case, one could securely use any model and data from any party under the MPC framework.

Both options are not satisfactory. In the first option, at least one of the two hospitals needs to share confidential data. In particular, data needs to be shared even if it turns out that no similar records exist. Moreover, if this option is done with multiple hospitals who each use their own model to compare two records, there is the risk that incomparable results are obtained. Consider, if a first data hospital reports two records which score a closeness of 0.1 and 0.3 respectively, and a second data hospital reports two records which score a closeness of 0.12 and 0.29 respectively. There is no telling which of these records are really the closest if the scales do not match exactly.

In the second option, no data needs to be shared in plain, but the MPC protocol would need to be repeated for all records in the data hospital. This is a prohibitively large computation.

There is a need to improve this situation.

SUMMARY OF THE INVENTION

A requesting device and a data device is proposed as defined in the claims. The requesting device can search for a record in a database stored in a data device, which is typically a remote device.

Interestingly, a target record at the requesting device and candidate records at the data device may be mapped to similarity values. A set of similarity values indicates how similar a given record is to a list of categories. The categories may represent common types of records, e.g., clusters of records. A set of similarity values is anonymizing, but still allows two records to be compared to each other. After a pre-filtering is done on the similarity values, a more precise evaluation using multi-party computation may be done.

A system comprising the proposed requesting device and data device preserves privacy since no records are exchanged in the plain, and multi-party computation is used to compare records. On the other hand the system is efficient since a filtering is done before using multi-party computation.

The proposed system may be used to find similar cases of a rare disease, while searching with privacy preservation. The system does not even require hospitals to reveal a data model that they have built from patient records of any patient directly. Moreover, it processes only a small number of patient records with multi-party computation, especially compared to the number of records in a hospital's database. Only relevant cases need to be compared in more detail using privacy-preserving techniques such as multi-party computation.

For example, as part of the MPC computation of the second closeness measure, the parties may compute cryptographic shares of the information in the target and selected candidate record respectively, and send a share of the information to the other party, e.g., to the other of the requesting and data device, another share is kept at the device where the record originates. For example, the shares may be computed on a per attribute basis. The MPC protocol may be computed on the shares. The outcome of the MPC protocol, e.g., the second closeness measure may be opened at the two devices, e.g., so that the outcome of the closeness computation is known to the two devices, but not the content of the records. For example, opening the outcome may be done by sending the share in the outcome that a party has, to the other party. Once a party has a share of the other party, it can open the corresponding value.

The requesting device and the data device are electronic devices; they may be computers. The requesting method and data method described herein may be applied in a wide range of practical applications. Such practical applications include patient records, product records, student records, and the like.

An embodiment of the method may be implemented on a computer as a computer implemented method, or in dedicated hardware, or in a combination of both. Executable code for an embodiment of the method may be stored on a computer program product. Examples of computer program products include memory devices, optical storage devices, integrated circuits, servers, online software, etc. Preferably, the computer program product comprises non-transitory program code stored on a computer readable medium for performing an embodiment of the method when said program product is executed on a computer.

In an embodiment, the computer program comprises computer program code adapted to perform all the steps of an embodiment of the method when the computer program is run on a computer. Preferably, the computer program is embodied on a computer readable medium. Another aspect of the invention provides a method of making the computer program available for downloading.

BRIEF DESCRIPTION OF THE DRAWINGS

Further details, aspects, and embodiments of the invention will be described, by way of example only, with reference to the drawings. Elements in the figures are illustrated for simplicity and clarity and have not necessarily been drawn to scale. In the Figures, elements which correspond to elements already described may have the same reference numerals. In the drawings, FIG. 1a, 1b, 1d schematically show an example of an embodiment of a requesting device, FIG. 1c, 1e schematically show an example of an embodiment of a data device, FIG. 1f schematically shows examples of an embodiment of an external database, FIG. 1g schematically shows an example of an embodiment of a requesting device and multiple data devices FIG. 2a schematically shows an example of an embodiment of a multi-party computation system for retrieving a record from a database, FIG. 2b schematically shows an example of an embodiment of a classifier for a requesting device and a classifier for a data device, FIG. 3 schematically shows an example of an embodiment of a data method, FIG. 4 schematically shows an example of an embodiment of are requesting method, FIG. 5a schematically shows a computer readable medium having a writable part comprising a computer program according to an embodiment, FIG. 5b schematically shows a representation of a processor system according to an embodiment.

LIST OF REFERENCE NUMERALS 100 a multiparty computation system
110 a requesting device
112 a communication interface
114 a storage
114' a database
114" an interfacing storage
116 a processor
118 a memory
120 a target record
122 a classifier
122.1-122.3 a sub-classifier
124 set of similarity values
124.1-124.3 a similarity value
126 a learning unit
136 a set of similarity values
138 multiple sets of similarity values
140 a selection unit
150 a MPC unit
160 a ranking unit
170 multiple categories
170.1-170-3 a category
210 a data device
210.1-210.3 a data device
212 a communication interface
214 a storage
214' a database
214" an interfacing storage
216 a processor
218 a memory
222 a classifier
222.1-122.3 sub-classifiers
224 a set of similarity values
226 a learning unit
230 a filtering unit
232 a candidate record
234 a set of similarity values
234.1-234.3 a similarity value
236 a selected candidate record
238 multiple selected candidate records
240 a selection unit
250 a MPC unit
1000 a computer readable medium
1010 a writable part
1020 a computer program
1110 integrated circuit(s)
1120 a processing unit
1122 a memory
1124 a dedicated integrated circuit
1126 a communication element
1130 an interconnect
1140 a processor system

DETAILED DESCRIPTION OF THE EMBODIMENTS

Figure 1A:
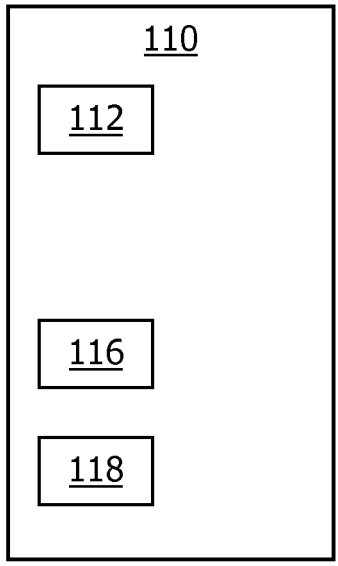

While this invention is susceptible of embodiment in many different forms, there are shown in the drawings and will herein be described in detail one or more specific embodiments, with the understanding that the present disclosure is to be considered as exemplary of the principles of the invention and not intended to limit the invention to the specific embodiments shown and described.

In the following, for the sake of understanding, elements of embodiments are described in operation. However, it will be apparent that the respective elements are arranged to perform the functions being described as performed by them.

Further, the invention is not limited to the embodiments, and the invention lies in each and every novel feature or combination of features described herein or recited in mutually different dependent claims.

FIG. 1a schematically shows an example of an embodiment of a requesting device 110. Requesting device 110 comprises a communication interface 112, a processor 116 and a memory 118. For example, memory 118 may comprise software and/or date on which processor 116 is configured to act. Processor 116 may be implemented as one or more processor circuits, e.g. microprocessors, ASICs, FPGA and the like. Memory 118 may comprise computer program instructions which are executable by processor 116. Processor 116, possibly together with memory 118 is configured according to an embodiment of a requesting device.

Figure 1B:
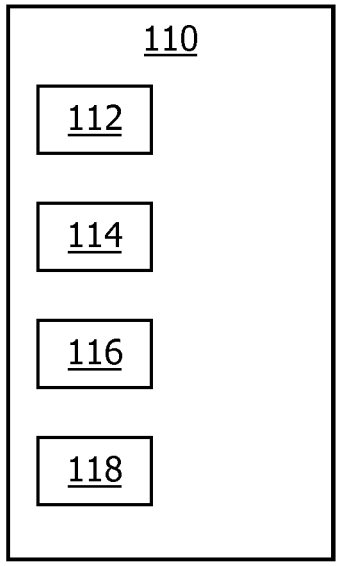
Figure 1C:
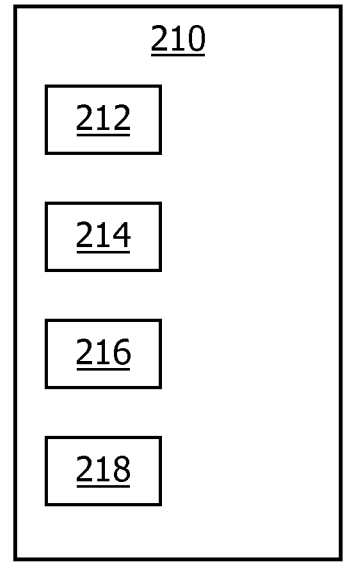

FIG. 1c schematically shows an example of an embodiment of a data device 210. Requesting device 210 comprises a communication interface 212, a processor 216 and a memory 218. Processor 216 may be implemented as one or more processor circuits, e.g. microprocessors, ASICs, FPGA and the like. Like requesting device 110, processor 216 and/or memory 218 are configured according to an embodiment of a data device. Data device 210 further comprises a storage 214 configured to store a database. The database comprises multiple candidate records. Storage, in particular for the database, may be implemented locally, e.g., as local memory, hard disk, and the like, or externally, e.g., in the form of cloud storage, etc.

A requesting device and one or more data devices together form an embodiment of a multiparty computation system for retrieving a record from a database. One particular embodiment of a MPC system 100 according to an embodiment is shown explicated in detail with reference to FIG. 2a.

The various devices of system 100 may communicate with each other over a computer network. The computer network may be an internet, an intranet, a LAN, a WLAN, etc. The computer network may be the Internet. The computer network may be wholly or partly wired, and/or wholly or partly wireless. For example, the computer network may comprise Ethernet connections. For example, the computer network may comprise wireless connections, such as Wi-Fi, ZigBee, and the like. The requesting and data devices comprise a communication interface 112, 212 respectively which are arranged to communicate with other devices of system 100 as needed. For example, the communication interface may comprise a connector, e.g., a wired connector, e.g., an Ethernet connector, or a wireless connector, e.g., an antenna, e.g., a Wi-Fi, 4G or 5G antenna. The computer network may comprise known elements such as, e.g., a router, a hub, etc. Communication may be in the form of digital messages, e.g., send and received in electronic form.

The execution of the requesting and data device(s) are implemented in a processor, e.g., a processor circuit, examples of which are shown herein. FIG. 2a below shows functional units that may be functional units of the processors. For example, FIG. 2a may be used as a blueprint of a possible functional organization of the processor circuits. The processor is not shown separate from the units in FIG. 2a, but is shown in FIGS. 1a-1e. For example, the functional units shown in FIG. 2a may be wholly or partially implemented in computer instructions that are stored at device 110 and/or 210, e.g., in an electronic memory of device 110 and/or 210, and are executable by a microprocessor of device 110 or 210. In hybrid embodiments, functional units are implemented partially in hardware, e.g., as coprocessors, e.g., crypto coprocessors, and partially in software stored and executed on device 110 and/or 210.

A number of variants to device 110 and 210 of FIGS. 1a and 1c are described below. The embodiments described with reference to FIG. 2a may be adapted to these variants.

FIG. 1b schematically shows an example of an embodiment of a requesting device 110. Like data device 210, requesting device 110 also comprises a storage 114 configured to store a database. The database comprises multiple records. In an embodiment, a target record at requesting device 110 is compared to candidate records at one or more data devices. This means that in an embodiment a requesting device does not need a database. However, a database local at device 110 can be used to derive a classifier locally which is advantageous. For example, no sensitive or proprietary classifying information needs to be exchanged between the parties. A storage 114 at device 110 is however not needed.

Figure 1D:
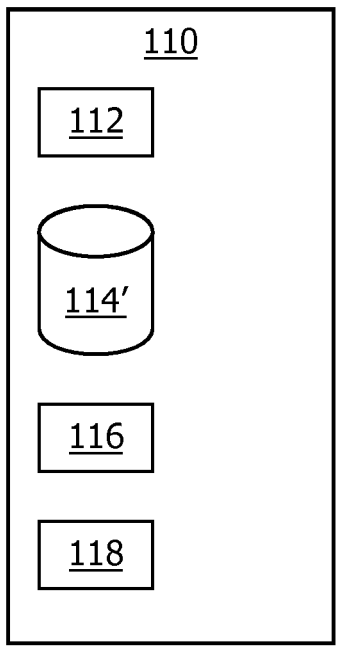
Figure 1E:
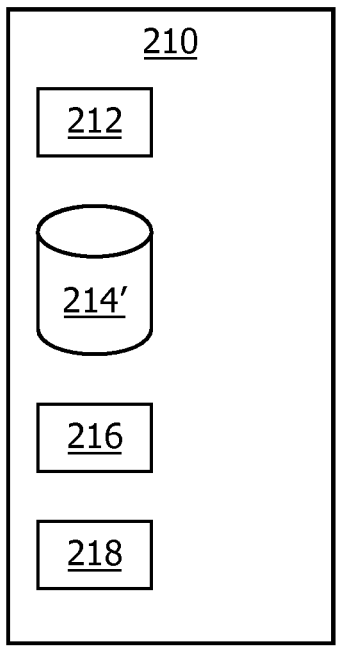
Figure 2A:
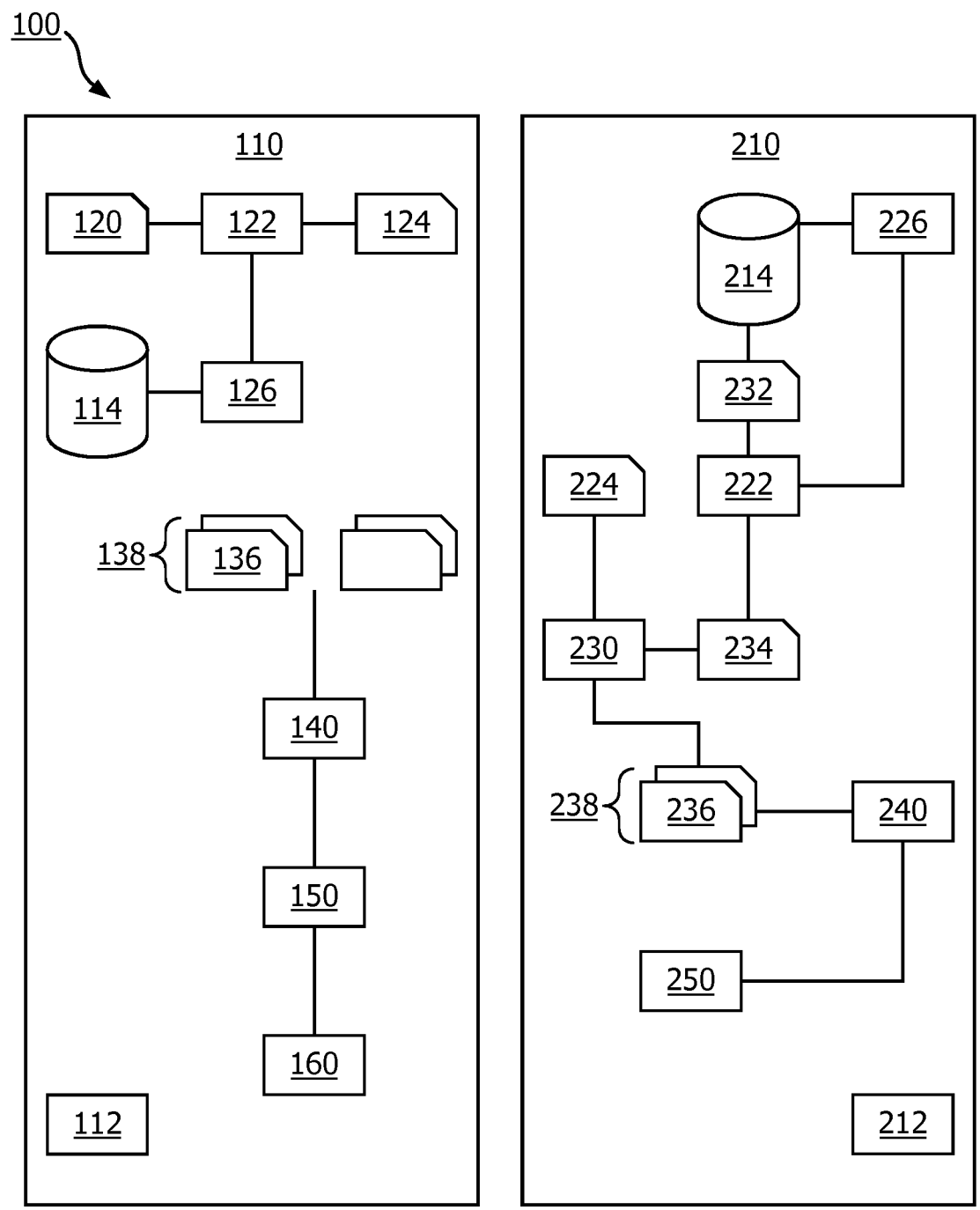

FIGS. 1d and 1e schematically show an example of an embodiment of a requesting device 110 and data device 210 in which the storage 114 and 214 is implemented as a locally stored database 114' and 214'.

Figure 1F:
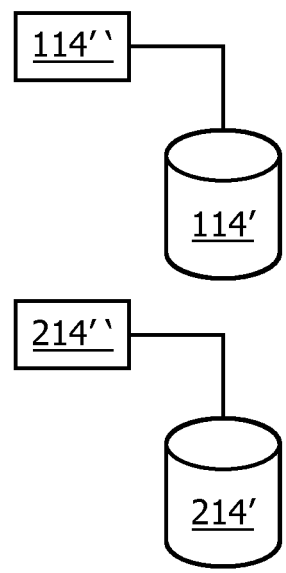

FIG. 1f schematically shows examples of an embodiment of an external database. Shown are an interfacing storage 114'' and interfacing storage 214'', which may be used as storage in device 110 and 210 respectively. The interfacing storages connect to an external database, e.g., in cloud storage. For example, when a record from a database is needed the interfacing storage may be asked for it, after which it may be retrieved, e.g., from the external database. The latter may be transparent to the rest of device 110 and/or 210.

Figure 1G:
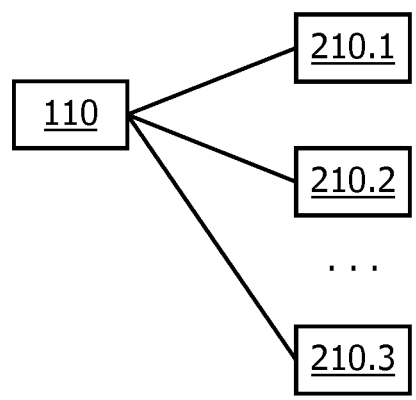

FIG. 1g schematically shows an example of an embodiment of a requesting device and multiple data devices. Shown are a single requesting device 110 and three data devices 210.1, 210.2, and 210.3. There may be two data devices or more than three. The multiple data device 210.1-210.3 may all have a similar design.

Any combination of a requesting device and one/or more data devices may be combined to form a MPC system.

FIG. 2a schematically shows an example of an embodiment of a multi-party computation system 100 for retrieving a record from a database. System 100 comprises a requesting device 110 and a data device 210. In the shown example, the devices each have a local database 114 and 214 respectively. However, any of these databases may be replaced by a non-local database. Moreover, the database 114 of device 110 may be omitted altogether.

As pointed out above, FIG. 2a shows functional elements which may be implemented by the processor. FIG. 2a also shows some data elements for the purpose of explication.

System 100 comprises a requesting device 110 configured for multi-party computation to select a close record from an external database 214. Database 214 is external to data device 110, e.g., data device does not have direct read access to database 214. Data device 210 does have access to database 214. Requesting device 110 has a target record 120, e.g., received over the communication interface or retrieved from its own database, etc. For example, a user of device 110 may be interested to know if similar records exist. If similar records exist in its own database 114, then he may simply compare target record 120 with the records in storage 114. However, to directly compare the target record 120 to the records in storage 214 is not possible since device 110 does not have read access to storage 214. Users of device 210 may not be willing to share storage 214 with device 110 for all kinds of reasons, in particular, for legal and/or privacy reasons.

As a motivating example, we will assume that the records concern patient histories. The patients may have diseases which are more or less common. There is a particular desire to find similar records for patients with rare diseases. There are other possibilities. For example, the records may represent school histories, and the system may look for similar students. For example, the records may represent usage histories of apparatuses and the system may look for similar failure modes, etc. We will use the patient records and diseases as a motivating example, but keeping in mind that the underlying technology may easily be adapted to other situations in which a target record is to be compared to a non-local database of candidate records.

One solution which allows comparing two records without giving full read access to device 110 for storage 214 is to use multi party computations. For example, given two records mpc protocols exist that can compare the two records, e.g. compute a distance. In practice any computer code with can compute a distance for two records, can be modified to work in a mpc setting. However, running a mpc protocol for a database quickly becomes prohibitively expensive. MPC protocols require a lot of resources, while storage 214 may easily comprise 100 or more, 1000 or more, etc., records.

Device 110 comprises a classifier 122 and device 210 comprises a classifier 222. Classifier 122 is applied to target record 120. Classifier 222 is applied to candidate records in storage 214, one of which is shown in FIG. 2*a* as candidate record 232. Candidate record 232 is taken from database 214 and may or may not turn out to be close to record 120.

Figure 2B:
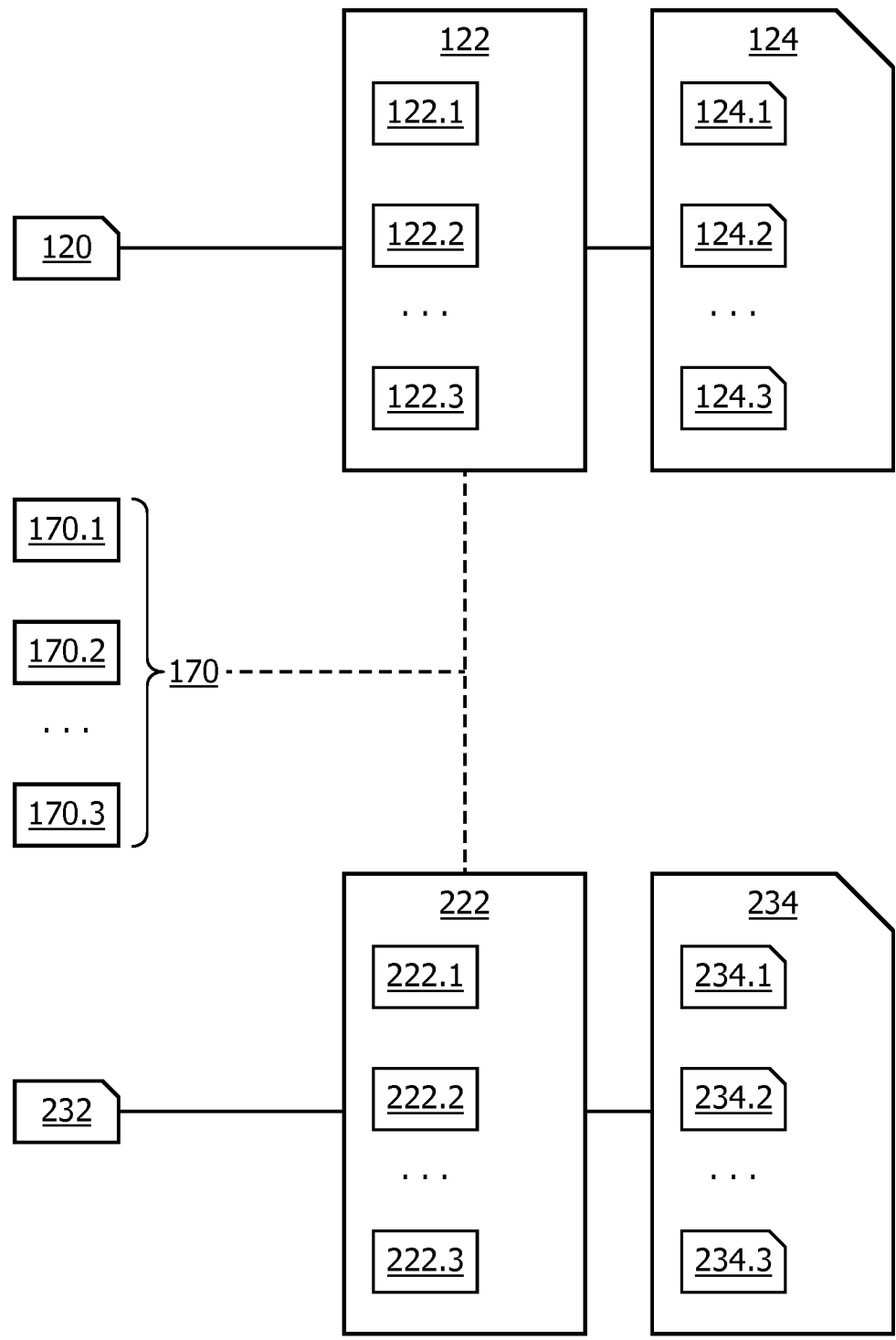

FIG. 2*b* schematically shows an example of an embodiment of a classifier for a requesting device and a classifier for a data device. FIG. 2*b* shows two records, a target record 120 at requesting device 110 and a candidate record 232 at data device 210. Two classifiers are shown: classifier 122 and classifier 222 also of requesting device 110 and data device 210 respectively.

A classifier such as classifiers 122 and 222 take a record as input and assign a set of similarity values to it, e.g., similarity measures; similarity sets 124 and 234 respectively. The similarity values indicate the likeness between the record and multiple categories. For example, the multiple categories may be common diseases and the records may be patient records. In this case the classifier indicates how like the various common diseases the records are. In an embodiment, there are 2 or more categories, 10 or more, 100 or more, etc.

In an embodiment, the mpc protocols are used to compare records, but the records are first filtered using the classifier. Both the target record and the candidate record are classified for the multiple categories. If the resulting similarity values are quite different then the original records do not need to be compared using the more expensive mpc since they are not close. If the resulting similarity values are alike, there is better possibility that the original records are also alike. The latter can be confirmed or further explored using mpc.

FIG. 2*b* shows one embodiment of classifiers. Shown in FIG. 2*b* are sub-classifiers 122.1-122.3 corresponding to classifier 122, and sub-classifiers 222.1-122.3 corresponding to classifier 222. A sub-classifier takes a record as input and assign a similarity value for one category of the multiple categories. For example, the classifiers may comprise one sub-classifier, for each category of the multiple categories. For example, FIG. 2*b* shows multiple categories 170 schematically, comprising categories 170.1, 170.2, and 170.3. There may be more or fewer categories. For example, similarity set 124 comprises similarity values 124.1, 124.2, 124.3, etc., corresponding to sub-classifiers 122.1, 122.2, 122.3, etc. The same for similarity set 234.

Preferably, the similarity sets are ordered. For example, they may be vectors. For example in a similarity vector particular entries in the vector correspond with particular categories. For example, a similarity vector may be (0.8, 0.2, 0.7) to indicate that the record had a 0.8 similarity to a category 1, say 170.1; 0.2 similarity to a category 2, say 170.2; etc. For example, the set may be lists of attributes. For example the same set may be represented as (cat3:0.7, cat1:0.8, cat2:0.2). In this case values are tagged with the corresponding category. The set may, but need not, be ordered.

Preferably, an entry in a similarity set has a corresponding entry in another similarity set, e.g., the entry corresponding to the same category. Some deviations from this rule may be tolerated however.

Advantageously, categories 170 are common categories to which records belong, e.g., have a high similarity with. Even records that do not belong to these categories may have a similarity with them. For example, categories may correspond to Liveborn, Septicemia, and Osteoarthritis. These were the three most common conditions listed as the principal diagnosis for hospital inpatient stays for 2015. (See, "HCUP Fast Stats. Healthcare Cost and Utilization Project (HCUP)", November 2017. Agency for Healthcare Research and Quality, Rockville, MD.) In this example, an attribute in a record of say patient-reported pain may contribute to similarity to all three conditions. However, patient-reported back-pain may contribute more to Osteoarthritis than to Septicemia.

There are a number of ways in which the classifiers may be obtained in devices 110 and 210. For example, the classifiers may be hand crafted. For example, they may be rule based and/or symptom based. For example, a category may have a number of associated conditions. If all conditions are satisfied, the record can be classified. A similarity value may be obtained by counting the number of satisfying conditions. In this case, the classifier may be obtained from a third party and acquired both for device 110 and 210. An advantage of this approach is that equal records will give equal similarity values, even though one is computed at device 110 and the other at device 210.

In an embodiment, the multiple categories at the data device and at the requesting device are the same. Moreover, comparing to similarity sets may comprise comparing the similarity values for corresponding categories. Note however that the categories themselves may be entirely implicit. For example, a classifier may produce a similarity vector without also giving information about which element corresponds to which category. Nevertheless, there is a relationship between the classifier of the two devices.

Interestingly, classifiers at the data device and at the requesting device may be different. As a result there may be slight deviations between sets of similarities computed at the requesting device 110 and the data device 210. In practice though, this turns out to be little cause for concern since the similarity sets are only used to pre-filter the records, to avoid doing expensive MPC protocols on records that are not likely to be matches. If it turns out that the classifiers at the two devices differ more than desired, one solution may be to increase the filtering threshold, so that more records are considered for MPC comparison.

One way in which the classifier may be obtained is by analyzing the records that are locally available. In an embodiment, the requesting device 110 comprises a learning unit 126 and/or data unit 210 a learning unit 226. The learning units 126, 226 are configured to analyze the data in storage 114 and 214 respectively to produce classifiers 122 and 222 respectively. This means that the two devices may provide their own classifiers. Producing a classifier may comprise producing parameters for a template classifier. The learning units are optional; it may be that none, or only device 110, or only device 210 comprises a learning unit.

For example, a learning unit may be configured to apply a clustering algorithm to the database of records at the data device and/or requesting device. The clusters may be assigned to categories of the multiple categories. A similarity value may be obtained, by computing the distance to a center or centroid of a cluster. Generally speaking a closeness measure can be obtained by computing a distance and vice versa. A distance may be converted to a closeness value, e.g., by inverting it, but typically this is not even necessary.

They outcome of the clustering algorithm may be unlabeled. It is desirable to assign categories to clusters, at least temporarily, so that the similarity values in the set correspond to each other. Assigning labels may be done manually, or it may be done automatically, for example, by using test records that are characteristic of the categories. For example, the device 110, and 210 may receive a test record, say for liveborn, Septicemia, etc., and use that to establish a link between clusters and categories. Another option is to use supervised learning in which at least part of the records in storage are pre-labeled. Yet another way to order the clusters does not use categories explicitly at all, neither during the learning phase nor during the execution phase. For example, the clusters obtained by the clustering algorithm may be ordered, e.g., by cluster size. The similarity sets may then also be ordered the same order. This approach works bests if the populations from which the records are drawn are similar, and the same distribution over the categories is expected. For example, the incidence of liveborn is more than twice that of septicemia, which is likely to be born out in any general hospital that were to perform the clustering analysis. Accordingly, by assigning a number of the largest diseases as the categories, which can be done locally without a pre-agreed set of categories, a reasonable correspondence between similarity sets can be established.

Returning to FIG. 2a. Requesting device 110 applies classifier 122 to target record 120 to obtain similarity set 124. For example, it may be suspected that target record 120 is not a common disease but actually a rare disease, which is why there is an interest in finding similarly afflicted persons. Requesting device 110 does not want to send target record 120 over to data unit 210, at least not at this moment. Instead, requesting device 110 sends over the similarity set 124 that is obtained for the target record. For example, the target record may be quite unlike liveborn, quite a bit like septicemia, and so on. On its own this information is not enough to establish what the disease is, especially not if the target record does not correspond with a common disease. This eventuality could be tested for if desired; for example requesting device 110 may refuse to send the similarity set for the target device if any of the similarity values exceed a threshold, say, exceed 0.9 on a scale of 0-1.

Data device 210 has a similarity set 224 which is received from requesting device 110. Typically similarity sets 124 and 224 are the same. Data device 210 comprises a filtering unit 230. Filtering unit is configured to perform a filtering of the candidate records in storage 214. Filtering unit 230 searches for candidate records for which their similarity set is close to the similarity set 224 received from requesting device 110. For example, filtering unit 230 may cause classifier 222 to be applied to the candidate records to obtain similarity sets for the candidate records in storage 214. This may be done on the spot, e.g., after a similarity set for a target record is received, but this is not necessary, for example, filtering unit 230 may be configured to precompute the set of similarity values for the candidate records.

Filtering unit 230 determines which of the similarity sets of candidate records are closed to the received similarity set 224 for the target record using a first closeness measure. The closeness measure takes as input two similarity sets and computes a number that indicates the closeness of the two sets. For example, if the similarity sets are vectors, this may be their Euclidian distance, it may be their cosine distance etc. Usually the two sets will be of equal size, e.g., because they were designed for the same multiple categories 170, but this is not necessary. For example, devices 110 and 210 may take a different number of common diseases into account. Say requesting device provides similarity values for 10 most common diseases, whereas the data device 210 has similarity values for the 20 most common diseases, or vice versa. This may be resolved, by discarding and/or zero-padding one or both of the similarity sets. Note that MPC protocols are not needed to compute the first closeness measures, since the data device 210 has all the data on which it is to be computed available in the plain. Accordingly, computing the first closeness measure is very efficient.

Since the two classifiers may be different, it is likely that even if the target record were identical to a candidate record, than still the similarity sets might not be identical. This is not a problem, since only a pre-filtering is done. Even if the two similarity sets are not equal, they will be close, which is sufficient. Filtering unit 230 may select one or more selected candidate records 238. For example, all records for which the first closeness measure is over a threshold may be selected; this may be implemented by selecting records for which a distance measure is below a threshold. For example, the top scoring records, e.g., the top 10, with respect to the first closeness measure may be selected. One selected record has reference number 236.

Data device 210 may be configured to perform a MPC protocol with requesting device 110 to jointly compute a second closeness measure between the target record and the selected candidate record. The second closeness measure is computed from data in the target record and in the selected candidate record. The second closeness measure is more accurate since it is computed from actual data in the records, rather than from data derived therefrom, in particular from the similarity values. Examples of second closeness measures are given below. Computing the second closeness value is more expensive than the first closeness value since a MPC protocol is needed. However, because of the filtering a number of second closeness computations are replaced by first closeness computations. This increases the efficiency of finding the close records in an external storage, e.g., storage 214.

Instead of directly deciding to perform a MPC protocol for candidate records that are selected on the basis of their first closeness measure, the selection can also be made by the requesting device. This is especially useful if the requesting device has made the request to multiple data devices. In an embodiment, data device 210 is configured to send the sets of similarity values for the selected candidates to requesting device 110. Requesting device 110 may be configured to receive sets of similarity values only from data device 210, but requesting device 110 may also be configured to receive similarity sets from multiple data devices. FIG. 2a shows that requesting device 110 has multiple similarity sets 138 received from data device 210 and/or other data devices. One of the received similarity sets has reference number 136. For example, set 136 may be the same as set 236. The similarity values obtained from different data device may not be exactly on the same scale, as they may be computed with different models; this is however no problem, so long as close records remain close enough to be selected for the second closeness measure computation. The latter computations may all be done using the same model, and thus produce comparable values.

Requesting device 110 comprises an optional selection unit 140. Selection unit 140 may be configured to receive similarity sets, possibly from multiple data devices, and to select the set of similarity values from the received sets of similarity values that are close to the set of similarity values of the target record. For example, the requesting device may use the first closeness measure for this. Selection unit 140 may use the computed first closeness measures to select the similarity sets that are most promising, e.g., closest. For example, in an embodiment, the similarity sets may have an associated identifier which may also be received by requesting device 110. The identifier may be selected by the data device in a way that does not reveal the originating candidate record. For example, the identifier may be selected randomly. Instead (or in addition) to sending and receiving the similarity sets themselves, the corresponding first closeness measures may be sent. The received and/or the computed first closeness values may be sorted by requesting device 110.

Requesting device 110 can then request a mpc protocol for one or more of the received similarity sets. Requesting device 110 may for example create a ranking based on the first closeness measure and do a mpc protocol for a number of the closest candidates, or for all candidates that are closer than a threshold.

For example, requesting device 110 may be configured to send a message to a data device 210, requesting a MPC protocol for one or more, or all of the similarity sets that were received from that data device. For example, requesting device 110 may send associated identifiers that were received with the similarity sets. For example, requesting device 110 may also send the received similarity sets to the data device to indicate that a MPC is needed for that particular set. The latter option has the advantage of avoiding the generating and bookkeeping of identifiers.

Selection unit 240 of data unit 210 may be configured to receive from requesting device 110 a request for a computation of the second closeness measure for at least one of the selected candidate records 238. Selection unit 240 retrieves from storage 214 of from set 238 the corresponding candidate record and initiates the mpc computation with the retrieved record.

Requesting device 110 may comprise a MPC unit 150. Data device 210 may also comprise a MPC unit 250. The MPC units 150 and 250 are configured to jointly performing a multiparty computation protocol with the requesting device to jointly compute a second closeness measure between the target record and the selected candidate record, the second closeness measure being computed from data in the target record and in the selected candidate record. If the requesting device works with multiple data device, then the other data devices may also have a MPC unit.

There are several ways of organizing a record, e.g., a target record and/or candidate record, so that they can be compared. For example, a general closeness measure such as the TFIDF distance measure may be used. A MPC protocol to compute such a distance is disclosed, e.g., in, "A Secure Protocol for Computing String Distance Metrics", by P. Ravikumar, et al.

For example, a record may comprises a list of attributes. For example, an attribute may be a measurement; it can be a value like temperature, and it can also be words that indicate a symptom, etc.

For example, in an embodiment, a record may comprise a list of (tag, value) pairs. The tag indicates the attribute-type, say 'age'. In the latter case, the value of the attribute may be 45, or it may be scaled, say 0.45, etc. To compare two records, first the attributes in the two records with the same tags are determined, and then a vector of the corresponding values may be constructed.

The MPC protocol may act on data which is secret-shared between the parties. For examples, the parties may submits secret-shares of their data to the other party, e.g., target and candidate record respectively. An example, of a secret-sharing system is so-called Shamir secret sharing. Another example of suitable MPC technology are garbled circuits. The MPC protocol may use the SPDZ protocol, e.g., to provide actively safe MPC.

For example, the MPC protocol may have two phases. In a first phase the intersection of attributes between the list of attributes in the target record and in the candidate record are determined. For example, to compute the intersection between the attributes, one may perform a so-called 'MPC private set intersection', for which various algorithms are known.

For example, the outcome of this phase may be a binary vector that indicates for each attribute in the target and/or candidate vector whether it is a joint attribute or not. The intersection vector may be shared, e.g., as a cryptographically shared secret, between the requesting device 110 and the data device 210. After it has been computed which attributes are in common, the second closeness measure may be computed from it in a second phase, e.g., from the associated values.

An efficient way to compute the second closeness value is to predetermine a finite list of allowed attributes that is shared between the requesting device and the data device. All attributes that are used are selected from the list. In this case, the attributes in a record can be represented as a binary vector. To determine the intersection of attributes in common one can compute a MPC, e.g., a computation on each of the vector's elements. Finally, a distance computation can be performed on the values of the intersected attributes.

For example, a record i may be represented as two vectors $a_i$ and $b_i$, wherein the first vector is a binary vector that indicates if the corresponding attribute is used, and wherein the second vector indicates the values of the used attributes. To compare two records i and j, one may first compute $a=a_i$ and $a_j$, then the vectors $a \cdot b_i$ and $a \cdot b_j$, wherein the 'and' and the multiplication are element wise. Finally, a distance, say Euclidean distance between the latter two vectors may be calculated. A larger distance being the same as a smaller closeness. The two vectors $a_i$ and $b_i$ may be encoded in a single vector, e.g., using the convention that a zero value indicates the absence of a vector and a non-zero value indicates the value.

If an attribute has a numerical value, then this value can be used in the distance computation directly, possibly after scaling. If the attributes values are words, then their similarity can be calculated, e.g., by checking a lookup table. The lookup table can give a predefined similarity between the pairs of words, e.g., pairs of symptoms.

There are many ways to calculate the closeness. A closeness based on Euclidean distance is the following example. The second closeness measure ($\rho$) of the target record and the candidate record may be computed as $$\rho = 1 - \frac{\|\tilde{x}_1 - \tilde{x}_2\|_2}{\|x_1\|_2 + \|x_2\|_2},$$

wherein $x_1$ and $x_2$ are the records to be compared, and the records restricted to the determined intersecting attributes are $\tilde{x}_1$ and $\tilde{x}_2$.

Below a number of further options and/or further embodiments are disclosed. The system may be used when a patient with rare a disease, sometimes referred to as a target disease, is received by the requesting hospital, sometimes referred to as the target hospital. A list of common diseases is inputted to both target hospital and Q candidate hospitals. The list of diseases is exemplifying for multiple categories.

The similarities between each patient record and the list of common diseases are computed at the various hospitals, e.g., at requesting and/or data devices. Interestingly, each hospital may compute this using its own data and algorithm. The vector of similarities between a record and the list of common diseases may be regarded as a new representation of the patient record. This new mapped features space is referred to as similarity space, and the mapped records as anonymized records. All data in the similarity space may be anonymized. Similarity values may be normalized, e.g., to be within a range, e.g., within [0,1].

In an embodiment, the target hospital, e.g., a requesting device, sends the anonymized target record to one or more candidate hospitals, e.g., data devices. The target hospital may request for M most similar cases from each candidate hospital. Each candidate hospital has clustered anonymized local data records, to determine its own model. The closeness between the similarity values for the target records and its own records are determined according to its own model. Each candidate hospital sends M most similar anonymized records to the target hospital. Thus, records are kept which are close to the target record according to the local cluster, e.g. according to the local model. The kept records can now be compared further with the target record in the original feature space using a multi-party computation technique. The rank of records is obtained based on this final comparison.

In a proposed system, a record of a rare disease is indicated as a target disease. Note that it is not necessary, for any of the participating hospitals to the label the target record with the rare disease. This is an advantage, labelling for rare diseases may not be supported by the local classifier, or may not be reliable. On the other hand there is a desire for doctors to know if other patients exist at other hospitals which have a similar record, e.g., which have similar attributes.

In order to get more accurate representation, the multiple categories, e.g. the list of common diseases may be arranged to have the following properties: 1) for each category, e.g., common disease the hospital has enough confidence to label/compare a record with; 2) these diseases should cover as many attributes, e.g., symptoms as possible to represent most of the diseases.

Here, we use d={$d_1$, . . . , $d_N$} to indicate a list of N common diseases. The feature mapping may be done as follows. Let a record with K attributes be x={$x_1$, . . . , $x_K$} the diagnostic model for disease $d_n$ in hospital i (Q candidate hospitals in total) is $\phi_{i,n}$, here we can consider SVM as the diagnostic model for explanation convenience; in practice, different hospitals may have different models for a specific disease. The similarity between record $x_j$ in hospital i and disease $d_n$ may be computed as $\hat{x}_{i,j,n}=\phi_{i,n}(x_j)$, where $\hat{x}_{i,j,n}$ is normalized to be within range [0,1], e.g. using Platt scaling. The vector $\hat{x}_{i,j}=\{\hat{x}_{i,j,1}, \ldots, \hat{x}_{i,j,N}\}$ is used as a new representation of a disease record in hospital i in the similarity space. In such a way, information like name, gender, date, detailed symptoms are anonymized without using MPC privacy preserving techniques. Note that, the number of attributes of different diseases in the same hospital may be different, while the number of attributes of the same disease in different hospitals may be different as well. The proposed system tackles this attribute dimension problem by transforming data into similarity space by using local models.

The similarity space may be used for a rough similar case searching. A rough list of potential similar cases in similarity space may thus be obtained. Interestingly, this may use local models, e.g., local clustering models. For example, establishing the closeness between a set of similarity values and local records in their own similarity space can be compared as follows. After transforming the records into similarity space, each hospital may apply a local clustering method on its local data $\hat{X}$. For example, one may use a hierarchical clustering method $\varphi$ with L2 norm to cluster the data into a number of clusters. Therefore, the closest neighbors/most similar records for each record can be found in the feature space. The target disease $\hat{x}_t$ may be sent to all the candidate hospitals, and M most similar records are required to feedback from these candidate hospitals. The M output records from hospital i can be computed by $\hat{X}_{i,M}=\varphi_i(\hat{X}_i,M)$. Note that, different hospitals may have different clustering models, therefore, the hospital models are secured because they are used locally with local data. The closeness of two records can be determined based on different clustering criteria. For example, here we use the L2 norm to calculate the closeness of two records in similarity space.

After collecting all the samples from all Q candidate hospitals (Q>=1), target hospital further compare these K*Q samples with its own clustering method by applying multi-party computation techniques. Considering the target hospital knows which hospital a record comes from, the received records can be easily located. Then, the target hospital compares a candidate record with the target disease in original feature space using MPC technique together with the corresponding candidate hospitals. For example, one may calculate the closeness of two records in the original feature space, then, the final ranking of the records can be sorted accordingly. Their corresponding diagnostic information/labels may be provided to target hospital/patient. Considering that the attribute dimension might be different from record to record, the closeness may be computed as follows: let $x_1$ and $x_2$ are the records to be compared, we select intersection attributes from these two attributes as $\tilde{x}_1$ and $\tilde{x}_2$. The final closeness ρ of these two records may be computed as $$\rho = 1 - \frac{\|\tilde{x}_1 - \tilde{x}_2\|_2}{\|x_1\|_2 + \|x_2\|_2}.$$

The higher the ρ is, the more similar the two records are.

The target hospital could train classifiers for the common diseases in list d, in order to have an early eliminate of a received record. The feature mapping process only needs to be done once, e.g., it may be precomputed for later use. If there are many relevant records from a particular hospital, then (doctor at) the target hospital may decide to ask for more relevant records from this particular hospital. Instead of asking for a fixed number of records, the number of records returned may also vary depending on the number of relevant matches found.

The proposed framework can also be used for automatic monitoring of hospital performance. With input of a random disease, the diagnostic results from all hospitals will be analyzed in an anonymized feature space without revealing patient information or hospital models. So that, the average/diversity/outlier of the diagnosis can be gained. Warning of incorrect diagnosis can be feedback to hospital automatically in a secured way.

Moreover, the proposed system actually can be generally applied in many places, using common anonymized category features.

In the various embodiments of the data device and requesting device, the communication interface may be selected from various alternatives. For example, the interface may be a network interface to a local or wide area network, e.g., the Internet, an application interface (API), etc.

The data device and requesting device may have a user interface, which may include well-known elements such as one or more buttons, a keyboard, display, touch screen, etc. The user interface may be arranged for accommodating user interaction for performing adding or retrieving records from storage, or to initiate a record retrieval.

Storage 114 and 214 may be implemented as an electronic memory, say a flash memory, or magnetic memory, say hard disk or the like. Storage 114 and 214 may comprise multiple discrete memories together making up storage 114 and 214. Storage 114 and 214 may also be implemented as a storage interface connecting with an external storage, e.g., cloud storage.

Typically, the requesting device and data device each comprise a microprocessor which executes appropriate software stored at the requesting device and data device; for example, that software may have been downloaded and/or stored in a corresponding memory, e.g., a volatile memory such as RAM or a non-volatile memory such as Flash. Alternatively, the requesting device and data device may, in whole or in part, be implemented in programmable logic, e.g., as field-programmable gate array (FPGA). The requesting device and data device may be implemented, in whole or in part, as a so-called application-specific integrated circuit (ASIC), e.g., an integrated circuit (IC) customized for their particular use. For example, the circuits may be implemented in CMOS, e.g., using a hardware description language such as Verilog, VHDL etc.

In an embodiment, the data device may comprise a communication circuit, a storage circuit, a processor circuit and a memory circuit. In an embodiment, the requesting device may comprise a communication circuit, a storage circuit, a processor circuit and a memory circuit. The requesting device may comprise one or more of a classifier circuit, a learning circuit, a selection circuit, a MPC circuit and a ranking circuit. The data device may comprise one or more of a learning circuit, a filtering circuit, a selection circuit, a MPC circuit. The circuits implement the corresponding units described herein. The circuits may be a processor circuit and storage circuit, the processor circuit executing instructions represented electronically in the storage circuits. The circuits may also be, FPGA, ASIC or the like.

The processor may be a processor circuit, which may be implemented in a distributed fashion, e.g., as multiple sub-processor circuits. A storage may be distributed over multiple distributed sub-storages. Part or all of the memory may be an electronic memory, magnetic memory, etc. For example, the storage may have volatile and a non-volatile part. Part of the storage may be read-only.

Figure 3:
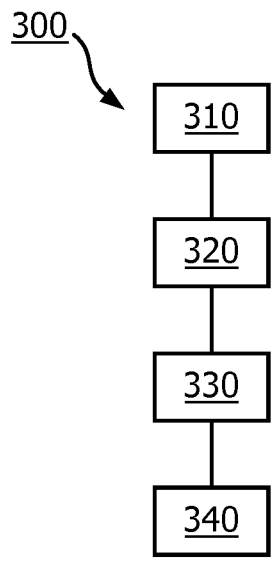

FIG. 3 schematically shows an example of an embodiment of a data method 300. Data method 300 is configured for multi-party computation to select a close record from a database. For example, data method 300 may be executed on a data device. Data method 300 comprises establishing 310 digital communication with a requesting device,
providing 320 a database, the database comprising multiple candidate records,
receiving 320 from the requesting device a set of similarity values between a target record and multiple categories, the set of similarity values being obtained by the requesting device by applying a classifier of the requesting device to the target record, a classifier assigning multiple similarity values between a record and the multiple categories,
performing 330 a filtering of the candidate records by selecting candidate records from the database for which the received set of similarity values for the target record are close to a set of similarity values between the selected candidate record and the multiple categories according to a first closeness measure computed from the set of similarity values for the target record and the set of similarity values for the selected candidate record, the set of similarity values for the selected candidate record being obtained by the candidate device by applying a classifier of the candidate device to the selected candidate record,—
for one or more selected candidate records,
performing 340 a multiparty computation protocol with the requesting device to jointly compute a second closeness measure between the target record and the selected candidate record, the second closeness measure being computed from data in the target record and in the selected candidate record.

Figure 4:
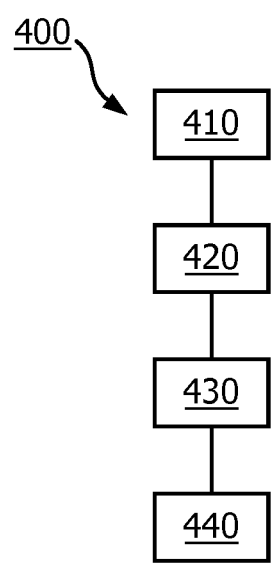

FIG. 4 schematically shows an example of an embodiment of are requesting method 400. Requesting method 400 is configured for multi-party computation to select a close record from an external database. Requesting method 400 comprises establishing 410 digital communication with a data device, the data device storing the external database, the database comprising multiple candidate records,
obtaining 420 a set of similarity values by applying a classifier of the requesting device to a target record, a classifier assigning multiple similarity values between a record and the multiple categories,
sending 430 the set of similarity values to the data device, the data device
performing a filtering of the candidate records by selecting candidate records from the database for which the set of similarity values for the target record are close to a set of similarity values between the selected candidate record and the multiple categories according to a first closeness measure computed from the set of similarity values for the target record and the set of similarity values for the selected candidate record, the set of similarity values for the selected candidate record being obtained by the candidate device by applying a classifier of the candidate device to the selected candidate record, and
for one or more selected candidate records,
performing 440 a multiparty computation protocol with the data device to jointly compute a second closeness measure between the target record and the selected candidate record, the second closeness measure being computed from data in the target record and in the selected candidate record.

Many different ways of executing the methods are possible, as will be apparent to a person skilled in the art. For example, the order of the steps can be varied or some steps may be executed in parallel. Moreover, in between steps other method steps may be inserted. The inserted steps may represent refinements of the method such as described herein, or may be unrelated to the method. Moreover, a given step may not have finished completely before a next step is started.

Embodiments of the method may be executed using software, which comprises instructions for causing a processor system to perform method 300 or 400. Software may only include those steps taken by a particular sub-entity of the system. The software may be stored in a suitable storage medium, such as a hard disk, a floppy, a memory, an optical disc, etc. The software may be sent as a signal along a wire, or wireless, or using a data network, e.g., the Internet. The software may be made available for download and/or for remote usage on a server. Embodiments of the method may be executed using a bitstream arranged to configure programmable logic, e.g., a field-programmable gate array (FPGA), to perform the method.

It will be appreciated that the invention also extends to computer programs, particularly computer programs on or in a carrier, adapted for putting the invention into practice. The program may be in the form of source code, object code, a code intermediate source, and object code such as partially compiled form, or in any other form suitable for use in the implementation of embodiments of the method. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth.

Figure 5A:
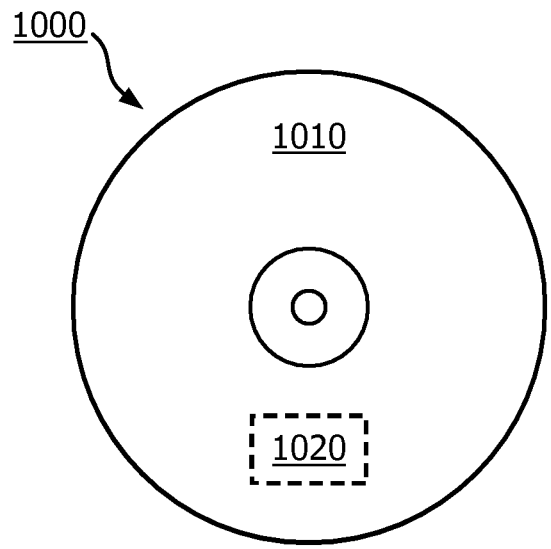

FIG. 5a shows a computer readable medium 1000 having a writable part 1010 comprising a computer program 1020, the computer program 1020 comprising instructions for causing a processor system to perform a requesting method and/or a data method, according to an embodiment. The computer program 1020 may be embodied on the computer readable medium 1000 as physical marks or by means of magnetization of the computer readable medium 1000. However, any other suitable embodiment is conceivable as well. Furthermore, it will be appreciated that, although the computer readable medium 1000 is shown here as an optical disc, the computer readable medium 1000 may be any suitable computer readable medium, such as a hard disk, solid state memory, flash memory, etc., and may be non-recordable or recordable. The computer program 1020 comprises instructions for causing a processor system to perform said requesting method and/or data method.

Figure 5B:
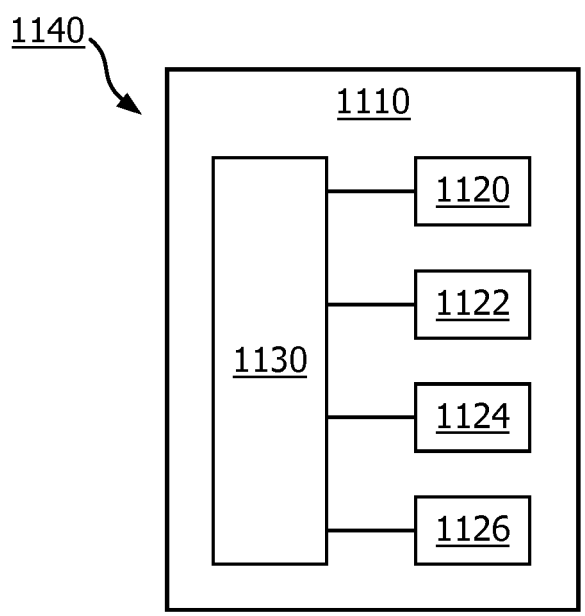

FIG. 5b shows in a schematic representation of a processor system 1140 according to an embodiment of a requesting device and/or a data device. The processor system comprises one or more integrated circuits 1110. The architecture of the one or more integrated circuits 1110 is schematically shown in FIG. 5b. Circuit 1110 comprises a processing unit 1120, e.g., a CPU, for running computer program components to execute a method according to an embodiment and/or implement its modules or units. Circuit 1110 comprises a memory 1122 for storing programming code, data, etc. Part of memory 1122 may be read-only. Circuit 1110 may comprise a communication element 1126, e.g., an antenna, connectors or both, and the like. Circuit 1110 may comprise a dedicated integrated circuit 1124 for performing part or all of the processing defined in the method. Processor 1120, memory 1122, dedicated IC 1124 and communication element 1126 may be connected to each other via an interconnect 1130, say a bus. The processor system 1110 may be arranged for contact and/or contact-less communication, using an antenna and/or connectors, respectively.

For example, in an embodiment, processor system 1140, e.g., the requesting device and/or the data device may comprise a processor circuit and a memory circuit, the processor being arranged to execute software stored in the memory circuit. For example, the processor circuit may be an Intel Core i7 processor, ARM Cortex-R8, etc. In an embodiment, the processor circuit may be ARM Cortex M0. The memory circuit may be an ROM circuit, or a non-volatile memory, e.g., a flash memory. The memory circuit may be a volatile memory, e.g., an SRAM memory. In the latter case, the device may comprise a non-volatile software interface, e.g., a hard drive, a network interface, etc., arranged for providing the software.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb 'comprise' and its conjugations does not exclude the presence of elements or steps other than those stated in a claim. The article 'a' or 'an' preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

In the claims references in parentheses refer to reference signs in drawings of exemplifying embodiments or to formulas of embodiments, thus increasing the intelligibility of the claim. These references shall not be construed as limiting the claim.

The invention claimed is:

1. A data device configured for multi-party computation to select a close record from a database, the data device comprising:
    a communication interface configured for digital communication with a requesting device,
    a storage configured to store the database, the database comprising multiple candidate records,
    a processor circuit configured to:
        receive from the requesting device a set of similarity values between a target record and multiple categories, the set of similarity values being obtained by the requesting device by applying a classifier of the requesting device to the target record, the classifier assigning multiple similarity values between a record and the multiple categories, wherein the classifier of the requesting device is derived at the requesting device by clustering a database of records of the requesting device,
        performing a filtering of the candidate records by selecting candidate records from the database for which the received set of similarity values for the target record are close to a set of similarity values between the selected candidate record and the multiple categories according to a first closeness measure computed from the set of similarity values for the target record and the set of similarity values for the selected candidate record, the set of similarity values for the selected candidate record being obtained by the data device by applying a classifier of the data device to the selected candidate record, wherein the classifier of the data device is derived at the data device by clustering the database of records of the data device, and for one or more selected candidate records,
performing a multiparty computation protocol with the requesting device, without giving full read access to the requesting device, to jointly compute a second closeness measure between the target record and the selected candidate record, the second closeness measure being computed from data in the target record and in the selected candidate record;
wherein the classifiers at the data device and at the requiring device are different.

2. The data device as in claim 1, wherein the multiple categories at the data device and at the requesting device are the same.

3. The data device as in claim 1, wherein multiple data devices select candidate records from multiple databases, the processor circuit of the data device being configured to
send to the requesting device the set of similarity values for the selected candidates and/or the corresponding first closeness measures,
receiving from the requesting device a request for a computation of the second closeness measure for at least one of the selected candidate records, wherein the multiparty computation protocol is performed with the requesting device for the requested selected candidate records.

4. The data device as in claim 1, wherein the processor circuit is configured to precompute the set of similarity values for the candidate records.

5. The data device as in claim 1, wherein a candidate record comprises a list of attributes.

6. The data device as in claim 5, wherein the multiparty computation protocol performed on the target record and a selected candidate record to compute the second closeness measure comprises:
determining the intersection of attributes between the list of attributes in the target record and in the candidate record, and computing the closeness from values for the determined intersecting attributes.

7. The data device as in claim 6, wherein the second closeness measure ($\rho$) of the target record and the candidate record is computed as:

$$\rho = 1 - \frac{\|\tilde{x}_1 - \tilde{x}_2\|_2}{\|x_1\|_2 + \|x_2\|_2}$$

wherein $x_1$, and $x_2$, are the records to be compared, and the records restricted to the determined intersecting attributes $\tilde{x}_1$ and $\tilde{x}_2$.

8. The data device as in claim 1, wherein the categories comprise diseases, and wherein the target record and candidate records comprise patient data.

9. A requesting device configured for multi-party computation to select a close record from an external database, the requesting device comprising:
a communication interface configured for digital communication with a data device, the data device storing the external database, the database comprising multiple candidate records,
a processor circuit configured to:
obtaining a set of similarity values by applying a classifier of the requesting device to a target record, a classifier assigning multiple similarity between a record and the multiple categories, wherein the classifier of the requesting device is derived at the requesting device by clustering a database of records of the requesting device,
sending the set of similarity values to the data device, the data device performing a filtering of the candidate records by selecting candidate records from the database for which the set of similarity values for the target record are close to a set of similarity values between the selected candidate record and the multiple categories according to a first closeness measure computed from the set of similarity values for the target record and the set of similarity values for the selected candidate record, the set of similarity values for the selected candidate record being obtained by the data device by applying a classifier of the data device to the selected candidate record, wherein the classifier of the data device is derived at the data device by clustering the database of records of the data device, and
for one or more selected candidate records,
performing a multiparty computation protocol with the data device, without having full read access to the data device, to jointly compute a second closeness measure between the target record and the selected candidate record without sharing the content of the records, the second closeness measure being computed from data in the target record and in the selected candidate record,
wherein the classifiers at the data device and at the requiring device are different.

10. The requesting device as in claim 9, wherein
the communication interface is configured for digital communication with multiple data devices, the processor circuit being configured to
receive from the multiple data devices a set of similarity values for the selected candidates and/or the corresponding first closeness measures,
selecting the set of similarity values from the set of similarity values received from the multiple data devices close to the set of similarity values of the target record according to the first closeness measure, and
performing the multiparty computation for the selected candidates corresponding to the selected set of similarity values.

11. A data method configured for multi-party computation to select a close record from a database, the data method comprising:
establishing digital communication with a requesting device,
providing a database, the database comprising multiple candidate records,
receiving from the requesting device a set of similarity values between a target record and multiple categories, the set of similarity values being obtained by the requesting device by applying a classifier of the requesting device to the target record, a classifier assigning multiple similarity values between a record and the multiple categories, wherein the classifier of the requesting device is derived at the requesting device by clustering a database of records of the requesting device,
performing a filtering of the candidate records by selecting candidate records from the database for which the received set of similarity values for the target record are close to a set of similarity values between the selected candidate record and the multiple categories according to a first closeness measure computed from the set of similarity values for the target record and the set of similarity values for the selected candidate record, the set of similarity values for the selected candidate record being obtained by the data device by applying a classifier of the data device to the selected candidate record, wherein the classifier of the data device is derived at the data device by clustering the database of records at the data device, for one or more selected candidate records,
  performing a multiparty computation protocol with the requesting device, without giving full read access to the requesting device, to jointly compute a second closeness measure between the target record and the selected candidate record, the second closeness measure being computed from data in the target record and in the selected candidate record, wherein the classifiers at the data device and at the requiring device are different.

12. A computer readable medium comprising non-transitory data representing instructions to cause a processor system to perform the method according to claim 11.

13. A requesting method configured for multi-party computation to select a close record from an external database, the requesting method comprising:
  establishing digital communication with a data device, the data device storing the external database, the database comprising multiple candidate records,
  obtaining a set of similarity values by applying a classifier of the requesting device to a target record, the classifier assigning multiple similarity values between a record and the multiple categories, wherein the classifier of the requesting device is derived at the requesting device by clustering the multiple candidate records of the database,
  sending the set of similarity values to the data device, the data device performing a filtering of the candidate records by selecting candidate records from the database for which the set of similarity values for the target record are close to a set of similarity values between the selected candidate record and the multiple categories according to a first closeness measure computed from the set of similarity values for the target record and the set of similarity values for the selected candidate record, the set of similarity values for the selected candidate record being obtained by the data device by applying a classifier of the data device to the selected candidate record, wherein the classifier of the data device is derived at the data device by clustering the database of records at the data device, and
  for one or more selected candidate records,
    performing a multiparty computation protocol with the data device, without giving full read access to the requesting device, to jointly compute a second closeness measure between the target record and the selected candidate record, the second closeness measure being computed from data in the target record and in the selected candidate record;
  wherein the classifiers at the data device and at the requiring device are different.

* * * * *